United States Patent [19]

Kondo et al.

[11] Patent Number: 4,576,705

[45] Date of Patent: Mar. 18, 1986

[54] APPARATUS WITH POLAROGRAPHIC SENSOR TO DETECT CONCENTRATIONS OF PLURALITY OF GAS COMPONENTS

[75] Inventors: Haruyoshi Kondo; Hideaki Takahashi; Keiichi Saji; Takashi Takeuchi; Kiyoharu Hayakawa, all of Aichi, Japan

[73] Assignee: Kabushiki Kaisha Toyota Chuo Kenkyusho, Aichi, Japan

[21] Appl. No.: 613,969

[22] Filed: May 24, 1984

[30] Foreign Application Priority Data

May 26, 1983 [JP] Japan .................................. 58-91441

[51] Int. Cl.$^4$ ........................................... G01N 27/48
[52] U.S. Cl. .................................. 204/406; 204/425; 204/426; 204/429; 123/440; 123/489
[58] Field of Search ............... 204/406, 408, 421, 424, 204/425, 426; 123/438, 440, 437, 489; 422/90, 98

[56] References Cited

U.S. PATENT DOCUMENTS

| | | | |
|---|---|---|---|
| 3,208,926 | 9/1965 | Eckfeldt | 204/409 X |
| 3,860,498 | 1/1975 | Jones | 204/425 X |
| 4,408,584 | 10/1983 | Yabuhara et al. | 123/489 X |
| 4,472,262 | 9/1984 | Kondo et al. | 204/426 X |

Primary Examiner—John F. Niebling
Assistant Examiner—Nam X. Nguyen

[57] ABSTRACT

An apparatus for detecting concentrations of a plurality of gas components has a single polarographic sensor capable of detecting an oxygen concentration and a composite concentration of oxygen gas, carbon dioxide gas and steam. A first voltage is applied to the polarographic sensor which then measures only the oxygen concentration, or a second voltage is applied to the sensor which then measures only the composite concentration of oxygen gas, carbon dioxide gas and steam. The first and second voltages are applied to the sensor in a time division manner. Upon application of first and second voltages in such a time division manner, corresponding currents flowing through the sensor are detected to obtain signals corresponding to the oxygen concentration and the composite concentration of oxygen gas, carbon dioxide gas and steam. The signal corresponding to the oxygen concentration is subtracted by an operational amplifier from the signal corresponding to the composite concentration of oxygen gas, carbon dioxide gas and steam, thereby obtaining a signal representing a composite concentration of carbon dioxide gas and steam.

11 Claims, 14 Drawing Figures

|  | $CO_2 + H_2O$ CONCENTRATION | | | |
|---|---|---|---|---|
|  | 0 [%] | 10 [%] | 20 [%] | 30 [%] |
| $O_2$ CONCENTRATION 0 [%] | a | b | c | d |
| $O_2$ CONCENTRATION 5 [%] | e | f | g | h |
| $O_2$ CONCENTRATION 10 [%] | i | j | k | l |

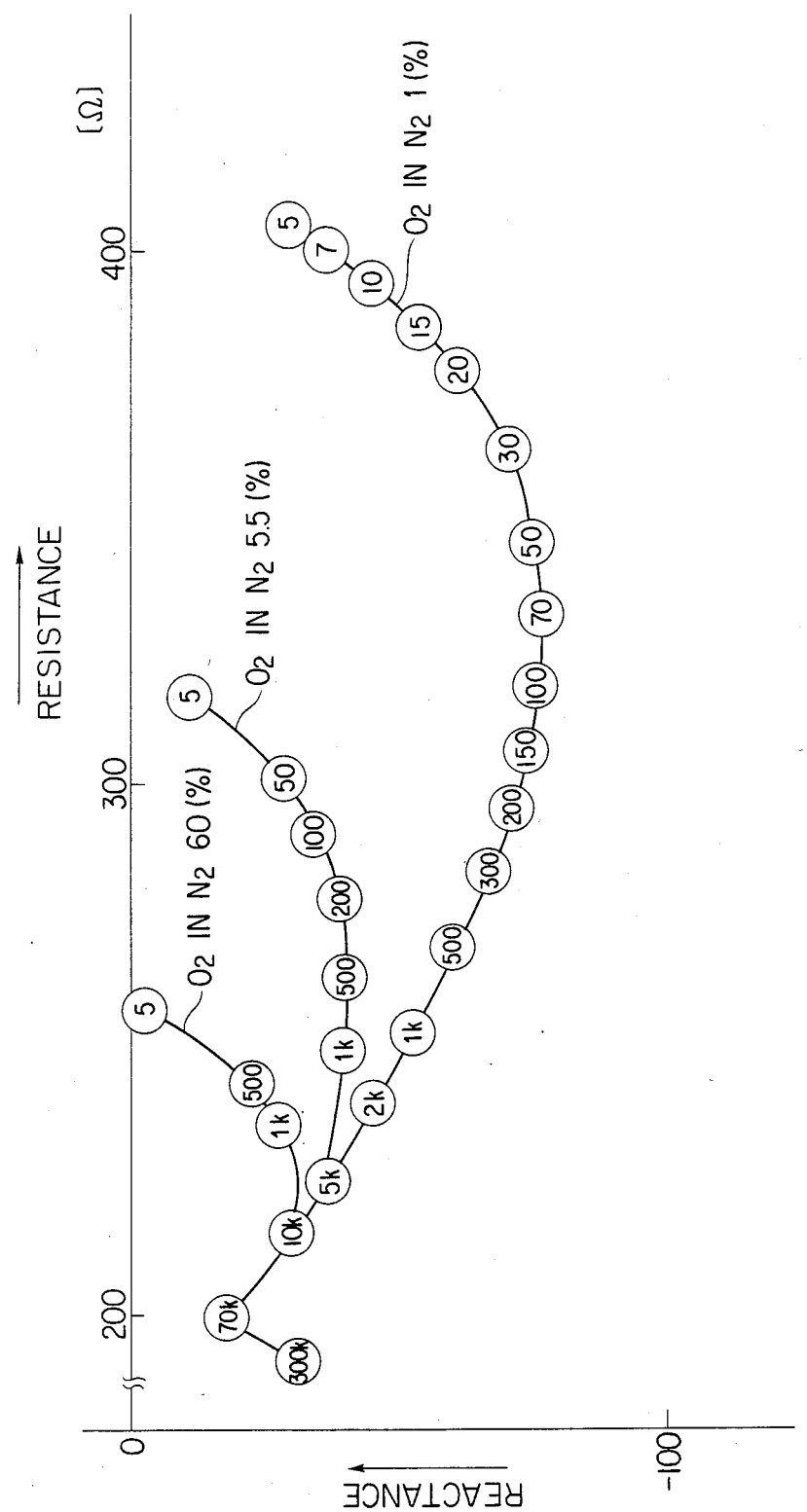

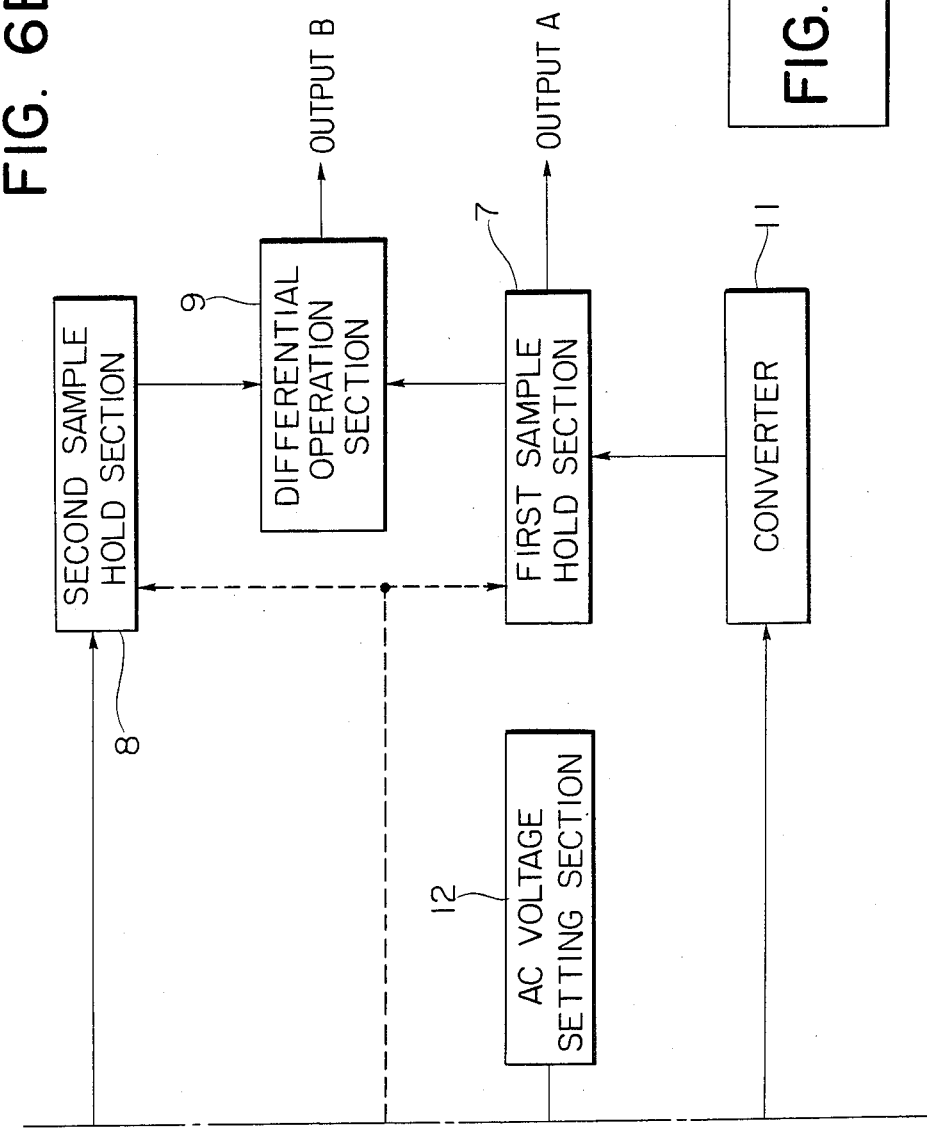

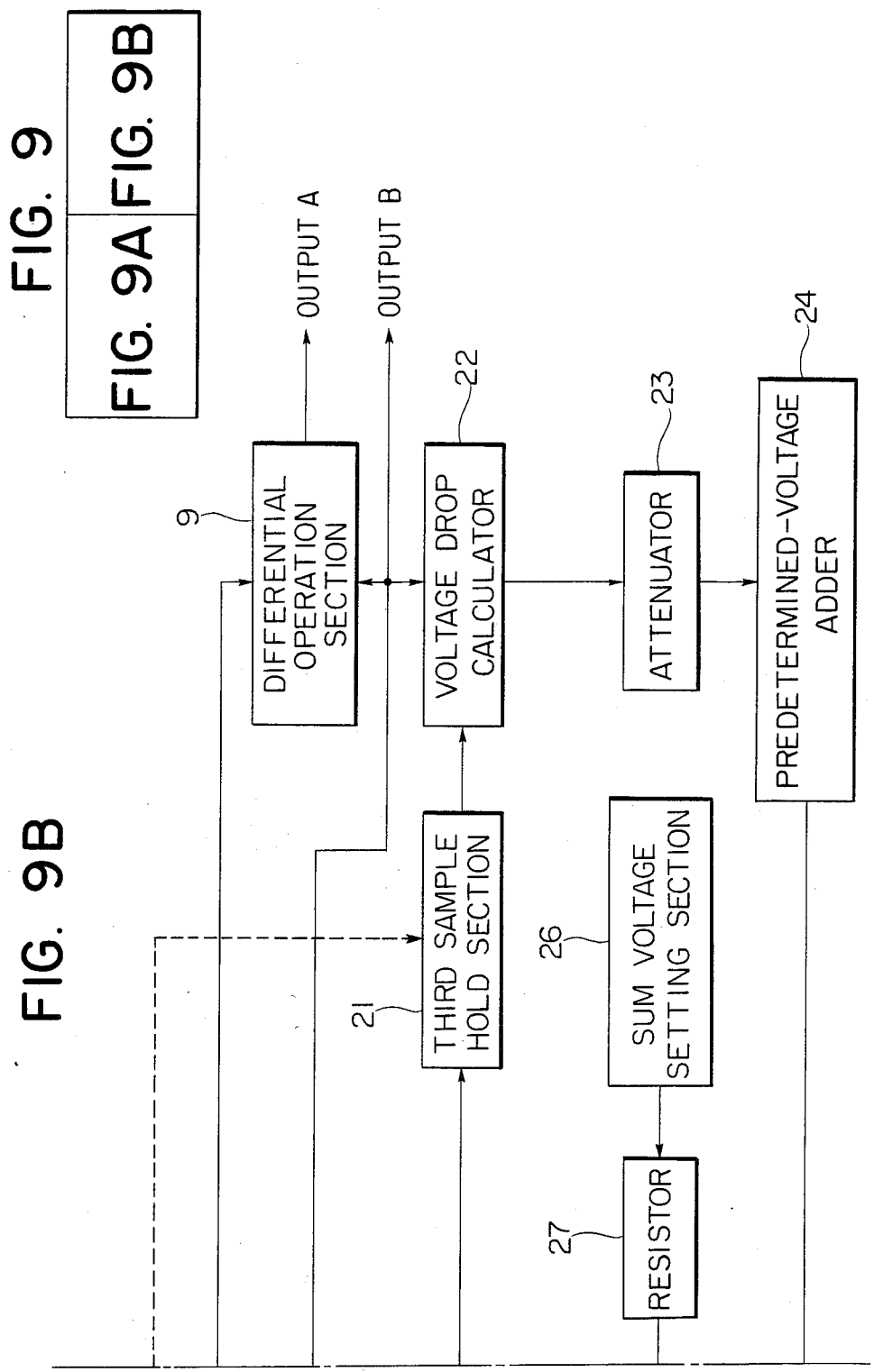

APPARATUS WITH POLAROGRAPHIC SENSOR TO DETECT CONCENTRATIONS OF PLURALITY OF GAS COMPONENTS

BACKGROUND OF THE INVENTION

I. Field of the Invention

The present invention relates to a concentration detecting apparatus using a polarographic sensor to detect or measure concentrations of a plurality of gas components.

II. Description of the Prior Art

Steam ($H_2O$) and carbon dioxide gas ($CO_2$) are produced by plants and animals, including man at various levels depending on activity. The measurement of $H_2O$ and $CO_2$ content is performed in plant cultivation, ethological/zoogeographic control and so on to provide information about the degree of activity of plants and animals. A plant cultivation system (vegetable cultivation system) for stably producing fresh, pesticide-free crops (mainly vegetables) all year around by an industrial means has received a great deal of attention. Such a vegetable cultivation system has been developed mainly in Europe and the United States of America. Ecological environments are artificially controlled in such a plant cultivation system to produce crops irrespective of changes in natural environments. According to this system, a great amount of energy must be inevitably used, so that a high yield must be obtained to satisfy the high energy consumption. For this reason, optimal plant cultivation conditions must be found, and ecological control must be performed to maintain these optimal conditions.

In such a plant cultivation system (i.e., factory), carbon dioxide gas has a high concentration of about 1,000 ppm. The level of sunshine, temperature, humidity, the content of carbon dioxide gas, the quality and quantity of water, air circulation, leaf temperature and so on are monitored by sensors, and are controlled by a computer.

In this field, concentrations of oxygen gas, steam and carbon dioxide gas must all be continuously monitored. For this purpose, demand for a compact, low-cost apparatus has arisen.

A multi-collector type mass analyzer or the like is used to measure ecosystem factors such as photosynthesis, respiration, evaporation and translocation which contribute to the growth of plants. This analyzer can highly precisely measure gas components such as carbon dioxide gas, oxygen gas and steam which are absorbed in and/or exhausted from the plants. However, the mass analyzer is large in size and expensive.

Another conventional system is employed to measure concentrations of a plurality of gases. Separate sensors are used to measure the concentrations of oxygen gas, carbon dioxide gas and steam. For example a limiting electric current type oxygen sensor is used to measure a concentration of oxygen gas; a thermal conduction type sensor is used to measure a concentration of carbon dioxide gas; and an absolute humidity sensor is used to measure a concentration of steam. According to this system, a plurality of sensors are required, resulting in high cost, a large installation space, heavy weight, and cumbersome manipulation.

In addition, when the concentrations of different gases are separately measured as described above, various types of carbon dioxide sensors may be used. However, none of them can satisfy the prescribed requirements. For example, a carbon dioxide gas measuring infrared ray analyzer has a large size and high cost, a solution absorbing type sensor has a slow response time and a sensor tube cannot perform continuous measurement.

SUMMARY OF THE INVENTION

The present invention has been made to solve the conventional problems described above.

It is an object of the present invention to provide an apparatus using a single polarographic solid electrolytic sensor to simultaneously detect an oxygen concentration and a composite concentration of oxygen gas, carbon dioxide gas and steam.

According to the present invention, there is provided an apparatus for detecting concentrations of a plurality of gas components, comprising: a polarographic solid electrolytic sensor; first voltage applying means for applying a first voltage to the polarographic sensor so that the polarographic sensor substantially measures only a concentration of oxygen gas; second voltage applying means for applying a second voltage to the polarographic sensor so that the polarographic sensor measures a composite concentration of oxygen gas, carbon dioxide gas and steam; electric signal detecting means for detecting electric signals from the polarographic sensor when the first and second voltages are applied to the polarographic sensor, respectively, and for generating a signal corresponding to the oxygen concentration and a signal corresponding to the composite concentration of oxygen gas, carbon dioxide gas and steam; and operating means for subtracting the signal corresponding to the oxygen concentration from the signal corresponding to the composite concentration of oxygen gas, carbon dioxide gas and steam, and for generating a signal corresponding to a composite concentration of carbon dioxide gas and steam.

An optimal value of the second voltage changes in accordance with changes in oxygen concentration, so that the second voltage can be controlled in response to the signal corresponding to the oxygen concentration.

Since the first and second voltages are selectively applied to the single polarographic sensor, a time division means can be used. According to an aspect of the present invention, the apparatus has a switching means for connecting the first voltage applying means to the polarographic sensor during a first period and the second voltage applying means to the polarographic sensor during a second period.

According to the aspect of the present invention, the switching means comprises a switching circuit and an alternating signal generator for controlling the switching circuit.

In order to perform an operation of output signals derived from the electric signal detecting means in a time division manner, the apparatus further comprises first sample holding means for storing data corresponding to the signal which corresponds to the oxygen concentration and is generated from the current detecting means during the first period, and second sample holding means for storing data corresponding to the signal which corresponds to the composite concentration of oxygen gas, carbon dioxide gas and steam and which is generated from the current detecting means during the second period.

The first and second voltages respectively comprise a DC or AC voltage. When a DC voltage is used as the first voltage, this DC voltage preferably falls within the range between 0.2 V and 0.8 V. On the other hand, when a DC voltage is used as the second voltage, this DC voltage preferably falls within the range between 1 V and 2 V.

When the first and second voltages are DC voltages, respectively, the first voltage is set to be a voltage obtained by adding a constant voltage and a voltage drop across the internal resistance of the polarographic sensor, and the second voltage is set to be a voltage obtained by adding the first voltage and a constant additional voltage supplied through a DC resistor, thereby compensating for the voltage drop across the internal resistance.

When an AC voltage is used as the first voltage, this AC voltage preferably falls within the range between 0.1 mV and 0.5 V. On the other hand, when an AC voltage is used as the second voltage, this AC voltage preferably falls within the range between 0.6 V and 1.4 V.

When the first voltage is an AC voltage, the current detecting means is constituted by a circuit for calculating an impedance of the polarographic sensor in accordance with the first voltage as the AC voltage and a detected AC current, and a converter for converting the impedance to the signal corresponding to the oxygen concentration. Similarly, when the second voltage is an AC voltage, the current detecting means is constituted by a circuit for calculating the impedance of the polarographic sensor in accordance with the second voltage as the AC voltage and a detected AC current, and a converter for converting a calculated impedance to the signal corresponding to the composite concentration of oxygen gas, carbon dioxide gas and steam.

The first voltage may be an AC voltage, and the second voltage may be an AC-DC superposed voltage obtained by superposing a DC bias voltage on the first voltage as the AC voltage.

BRIEF DESCRIPTION OF THE DRAWINGS

in FIG. 1A;

FIG. 4 is a graph showing the characteristics of the polarographic sensor when an AC voltage is applied thereto, and more particularly, the impedances of respective frequencies when the oxygen concentration in $N_2$ gas is used as a parameter, wherein numerals in circles respectively denote AC frequencies;

DETAILED DESCRIPTION OF THE INVENTION

A polarographic sensor is known as a limiting electric current type oxygen sensor. An anode and a cathode are formed on the surface of an ionic conductor which comprises a solid electrolyte, and a gas diffusion limiting member is formed on the cathode, as disclosed in Japanese Laid-Open Patent Application No. 57-192,850. The voltage-current characteristics of this polarographic sensor are given such that the voltage is substantially proportional to the current in a region (called a resistance control region) where the voltage is low and the current is small, but change in a current flow is small even if the voltage is increased in a voltage region (called an overpotential control region) and this current is called a limiting electric current. This limiting electric current is substantially proportional to the oxygen concentration. In a higher-voltage region than the overpotential control region, a current abruptly increases although the voltage is only slightly increased. This higher-voltage region is called an excess current region. In this manner, it is conventionally understood that the polarographic sensor can detect only one component (e.g., oxygen gas concentration).

However, when the characteristics of the polarographic sensor were examined in detail, it was found that the sensor could detect a plurality of components such as an oxygen gas concentration ($O_2$ concentration), a composite concentration of carbon dioxide gas ($CO_2$) and steam ($H_2O$).

Figures 1A, 1B:
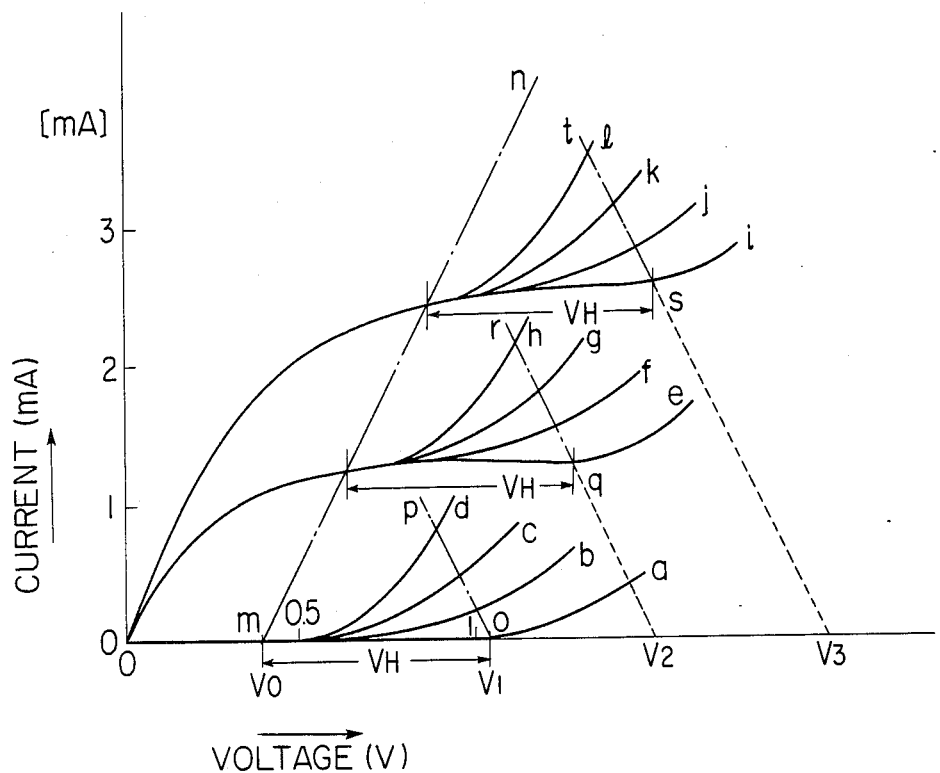
FIG. 1A is a graph showing the characteristics of a polarographic sensor used in an apparatus to detect concentrations of a plurality of gas components according to the present invention.
FIG. 1B is a table showing the relationship between the oxygen concentration and the composite concentration of carbon dioxide gas and steam so as to correspond to characteristic curves shown.

FIG. 1A shows the measurement results of the characteristics of the polarographic sensor by using gases containing nitrogen ($N_2$) gas as the major component and as additives oxygen ($O_2$) gas, carbon dioxide ($CO_2$) gas and steam ($H_2O$). More particularly, FIG. 1A shows the relationship between the applied voltage (abscissa) and the current (ordinate) when the respective gas components are used as parameters. Referring to FIG. 1A, in the region at a relatively low applied voltage, the current is determined by only the oxygen concentration. However, in the region at a relatively high applied voltage, the characteristic curve is branched into curves a to l in accordance with the $O_2 + CO_2 + H_2O$ concentration. FIG. 1B shows the relationship between oxygen concentrations and the $CO_2 + H_2O$ concentrations of the respective curves a to l of FIG. 1A.

As is apparent from the characteristics of the polarographic sensor, as shown in FIG. 1A, when a relatively low voltage is applied to the polarographic sensor, the $O_2$ concentration can be detected. On the other hand, when a relatively high voltage is applied to the polarographic sensor, the $O_2 + CO_2 + H_2O$ concentration can be detected. When the $O_2$ concentration is subtracted from the $O_2 + CO_2 + H_2O$ concentration, the $CO_2 + H_2O$ concentration is calculated.

Figure 2:
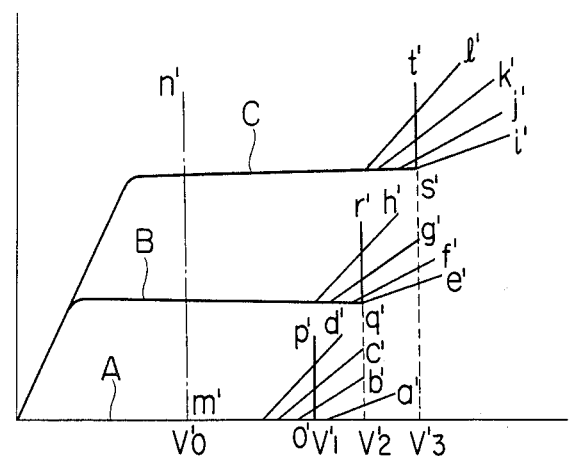
FIG. 2 is a graph for explaining the characteristics of FIG. 1A in a simplified manner.

This principle of the present invention will be described in more detail with reference to FIG. 2, which shows the characteristic curves of FIG. 1A in a simplified form. When a constant voltage $V_O'$ is applied to the polarographic sensor, a current in proportion to the $O_2$ concentration flows through the sensor, and this current is detected to measure the corresponding $O_2$ concentration. Voltages $V_1'$, $V_{2'}$, and $V_3'$, obtained at intersections of lines o'p', q'r' and s't' with branched portions (curves a' to l') changing in accordance with the $O_2 + CO_2 + H_2O$ concentration are selectively applied to the polarographic sensor. For example, when the $O_2$ concentration is given in accordance with the characteristic curve B, the voltage $V_2'$ given by line q'r' is applied to the polarographic sensor. When the voltage $V_2'$ has a level corresponding to branched curves e' to h' in accordance with the $O_2CO_2+H_2O$ concentration, a current corresponding to the voltage $V_2'$ is detected to measure the $O_2+CO_2+H_2O$ concentration. Similarly, when the $O_2$ concentration is given by the curve A or C, the corresponding voltage $V_1'$ or $V_2'$ is applied to the polarographic sensor. The voltages $V_1'$ to $V_3'$ for measuring the respective $O_2+CO_2+H_2O$ concentrations must be selectively used in accordance with the corresponding $O_2$ concentrations. However, the $O_2$ concentration is first detected, so that the applied voltage can be controlled in accordance with the detected $O_2$ concentration. The detected $O_2$ concentration is then subtracted from the detected $O_2+CO_2+H_2O$ concentration to calculate a $CO_2+H_2O$ concentration.

In the principle described above, the voltages applied to the polarographic sensor are given to be $V_0'$, $V_1'$, $V_2'$ and $v_3'$ represented by vertical lines m'n', o'p', q'r', and s't', respectively. However, since the actual characteristics of the polarographic sensor are given as shown in FIG. 1A and the possible measuring range becomes narrowed and measuring errors are increased upon application of the constant voltage, voltages are preferably applied to the sensor in practice, such that the operating points are given by inclined lines mn, op, qr and st, respectively. The technique for applying a voltage for measuring the $O_2$ concentration was disclosed in U.S. Ser. No. 373,257 entitled "Limiting Electric Current Type Oxygen Concentration Detecting Apparatus" by Kondo, Saji, Takeuchi et al, and filed on Apr. 29, 1982, wherein a voltage is applied such that the operating point is represented by the line mn. This technique can also be applied to the present invention. In order to obtain voltages for measuring the $O_2+CO_2+H_2O$ concentration along the inclined lines op, qr and st, any one of the voltages may be applied to the polarographic sensor through a constant resistance.

The present invention will be described in detail with reference to preferred embodiments thereof.

Figure 3:
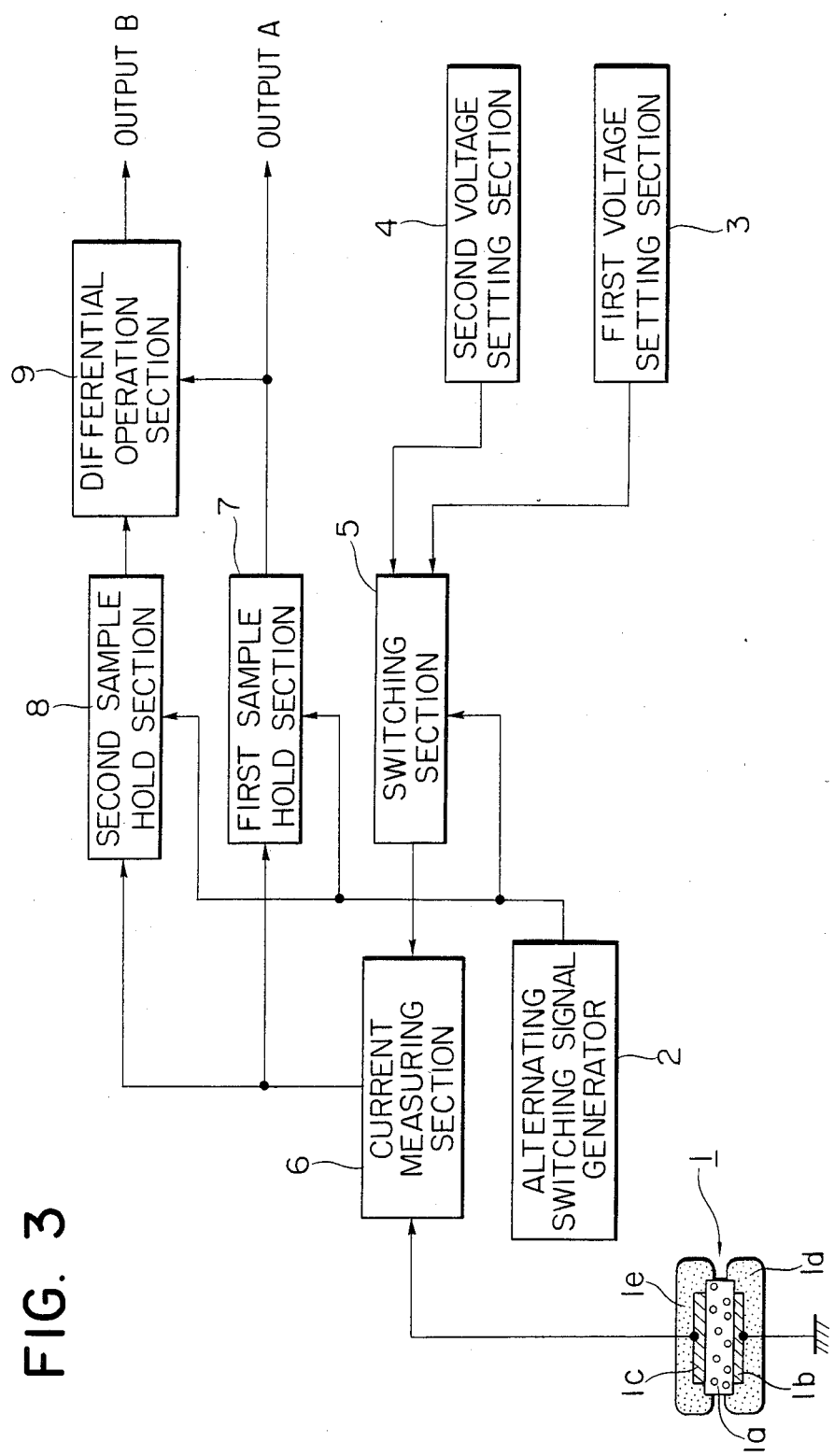
FIG. 3 is a block diagram of an apparatus using a polarographic sensor to detect concentrations of a plurality of gas components according to an embodiment of the present invention.

FIG. 3 is a block diagram showing the basic configuration of an apparatus using a polarographic sensor to detect concentrations of a plurality of gas components according to an embodiment of the present invention. This apparatus includes: a polarographic sensor 1; an alternating switching signal generator 2, a first voltage setting section 3 for applying a voltage to the polarographic sensor 1 which then measures only the $O_2$ gas concentration so as to generate a current corresponding to an $O_2$ concentration; a second voltage setting section 4 for applying a voltage to the sensor 1 which then measures only the $O_2+CO_2+H_2O$ concentration so as to generate a current of the corresponding concentration; a switching section 5 for switching the voltages generated from the first and second voltage setting sections 3 and 4 in response to a switching signal; a current detecting section 6 for detecting the current flowing through the sensor 1 in accordance with the voltage applied thereto; a first sample hold section 7 for holding a signal corresponding to the current when the voltage is applied from the first voltage setting section 3 to the sensor 1; a second sample hold section 8 for holding a signal corresponding to the current when the voltage is applied from the second voltage setting section 3 to the sensor 1; and an operation section 9 for subtracting the output of the first sample hold section 7 from that of the second sample hold section 8 and generating a signal corresponding to a $CO_2+H_2O$ gas concentration.

The polarographic sensor 1 comprises an oxygen ionic conductor 1a, a cathode 1b, an anode 1c, a case with pores 1d, and a protective coating layer 1e. In this embodiment, a flat sensor is exemplified, however, the present invention can also be applied to a cylindrical sensor with or without a bottom. In addition, the present invention can also be applied to a sensor which does not have a case with pores and which utilizes oxygen gas diffusion in the electrodes.

An output from the first voltage setting section 3 is the voltage capable of setting the operating point on the line mn of FIG. 1A. The technique disclosed in U.S. Ser. No. 373,257 can be used to generate the above voltage. More specifically, a voltage corresponding to a voltage drop across the internal resistance of the sensor is added to a constant voltage $V_0$. Therefore, the internal resistance of the sensor must be measured. For this purpose, a method is used wherein a very low voltage is applied to measure the internal resistance. Alternatively, a method is used wherein a sensor is arranged to measure only the internal resistance. When the internal resistance of the sensor is sufficiently low, the voltage drop across the internal resistance can be neglected. In this case, the inclined line mn can be replaced with the vertical line m'n' of FIG. 2. In other words, a constant voltage $V_0'$ can be applied to the sensor. In addition, since the internal resistance of the sensor need not be measured, the overall construction of the apparatus can be simplified.

The output from the second voltage setting section 4 corresponds to a voltage given by a line (e.g., op, qr or st) inclined counterclockwise. The voltage along the line op is obtained by applying a voltage $V_1$ through a resistor having a resistance corresponding to the inclined line op. Similarly, the voltages along the lines qr and st are obtained by applying voltages $V_2$ and $V_3$ through resistors having resistances corresponding to the inclined lines qr and st, respectively. It should be noted that the voltage $V_1$, $V_2$ or $V_3$ is generated from a variable voltage source which is controlled by the signal corresponding to a given $O_2$ concentration upon application of the voltage from the first voltage setting section to the sensor.

The voltages along the lines op, qr and st of FIG. 1A can be produced by utilizing the output generated from the first voltage setting section 3. As shown in FIG. 1A, the lines op, qr, st and so on correspond to the line inclined counterclockwise from the point where a predetermined constant voltage $V_H$ is added to the output (voltage along the line mn) generated from the first voltage setting section 3. Therefore, the second voltage setting section 4 comprises a constant voltage ($V_H$) supply and a resistor series-connected to this power supply. The output from the second voltage setting section 4 is superposed on the output generated from the first voltage setting section 3, thereby producing the desired voltage to be applied to the sensor.

The operation of the apparatus shown in FIG. 3 will now be described. The output from the first voltage setting section 3 is applied to the sensor 1 through the switching section 5, and a current flowing through the sensor 1 is then detected by the current detecting section 6. A value detected by the current detecting section 6 is held by the first sample hold section 7. This signal corresponds to the $O_2$ concentration and appears at an output terminal A.

Subsequently, the switching section 5 is operated to connect the second voltage setting section 4 and the sensor 1, and a current flowing through the sensor 1 is detected by the current detecting section 6. A value detected by the current detecting section 6 is held by the second sample hold section 8. This signal corresponds to the $O_2+CO_2+H_2O$ gas concentration. The operation section 9 subtracts the output of the first sample hold section 7 from the output of the second sample hold section 8 and generates a signal corresponding to a $CO_2+H_2O$ gas concentration. This signal appears at an output terminal B.

In the embodiment shown in FIG. 3, DC voltages are selectively applied to the polarographic sensor to measure the oxygen concentration and the composite concentration of oxygen gas, carbon dioxide gas and steam, and hence the concentration of carbon dioxide gas and steam. However, AC voltages may also be selectively applied to the polarographic sensor to measure the impedance of the sensor and hence the gas concentrations.

FIG. 4 is a graph showing changes in impedance of the sensor when the frequencies of AC voltages applied to the sensor are varied and the oxygen concentration is used as a parameter. The resistance is plotted along the abscissa, and the reactance is plotted along the ordinate. It should be noted that the sensor is operated at a voltage of 0.1 V and a temperature of 700° C. Encircled numerals plotted along the curves denote frequencies. The concentrations of oxygen contained in $N_2$ gas are set to be 1%, 5.5% and 60%, respectively.

Figure 5:
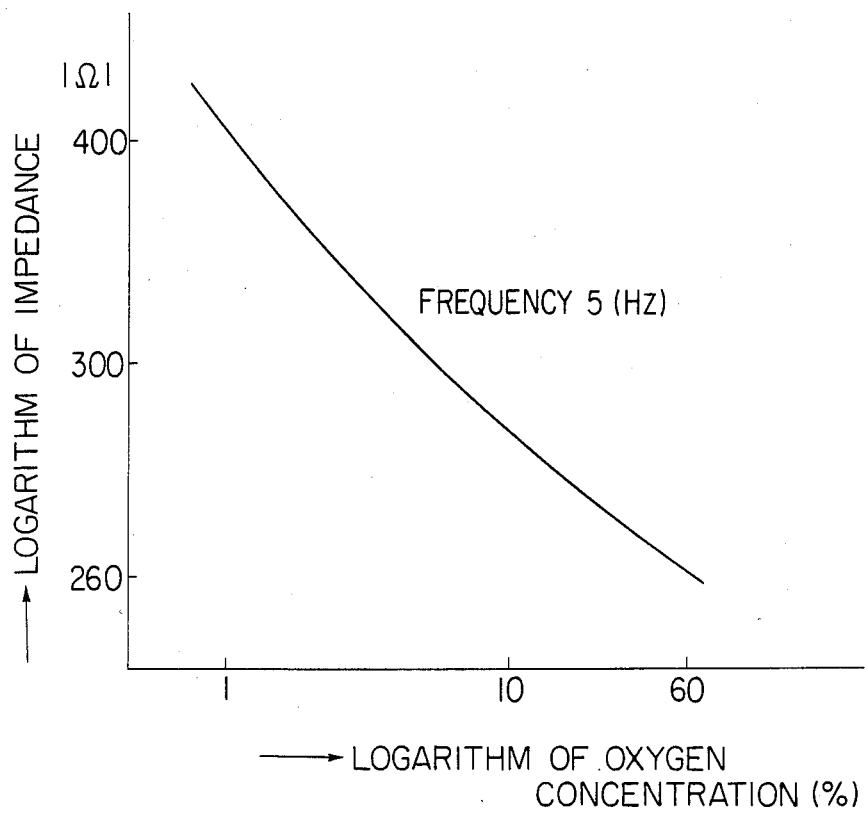
FIG. 5 is a graph showing the relationship between the oxygen concentration and the impedance when an AC voltage having a frequency of 5 Hz is applied to the sensor.

As is apparent from FIG. 4, different characteristic curves are obtained in accordance with corresponding oxygen concentrations. In particular, when the frequency is as relatively low as the range between 5 Hz and 1 kHz, the oxygen concentration changes so as to correspond to changes in resistance or reactance, or in the impedance as a combination of resistance and reactance. Therefore, the resistance component, the reactance component, the impedance, or inverse components (e.g., conductance, susceptance, admittance) thereof are measured to obtain the oxygen concentration. FIG. 5 is a graph showing the relationship between the oxygen concentration and the impedance.

Figure 6A:
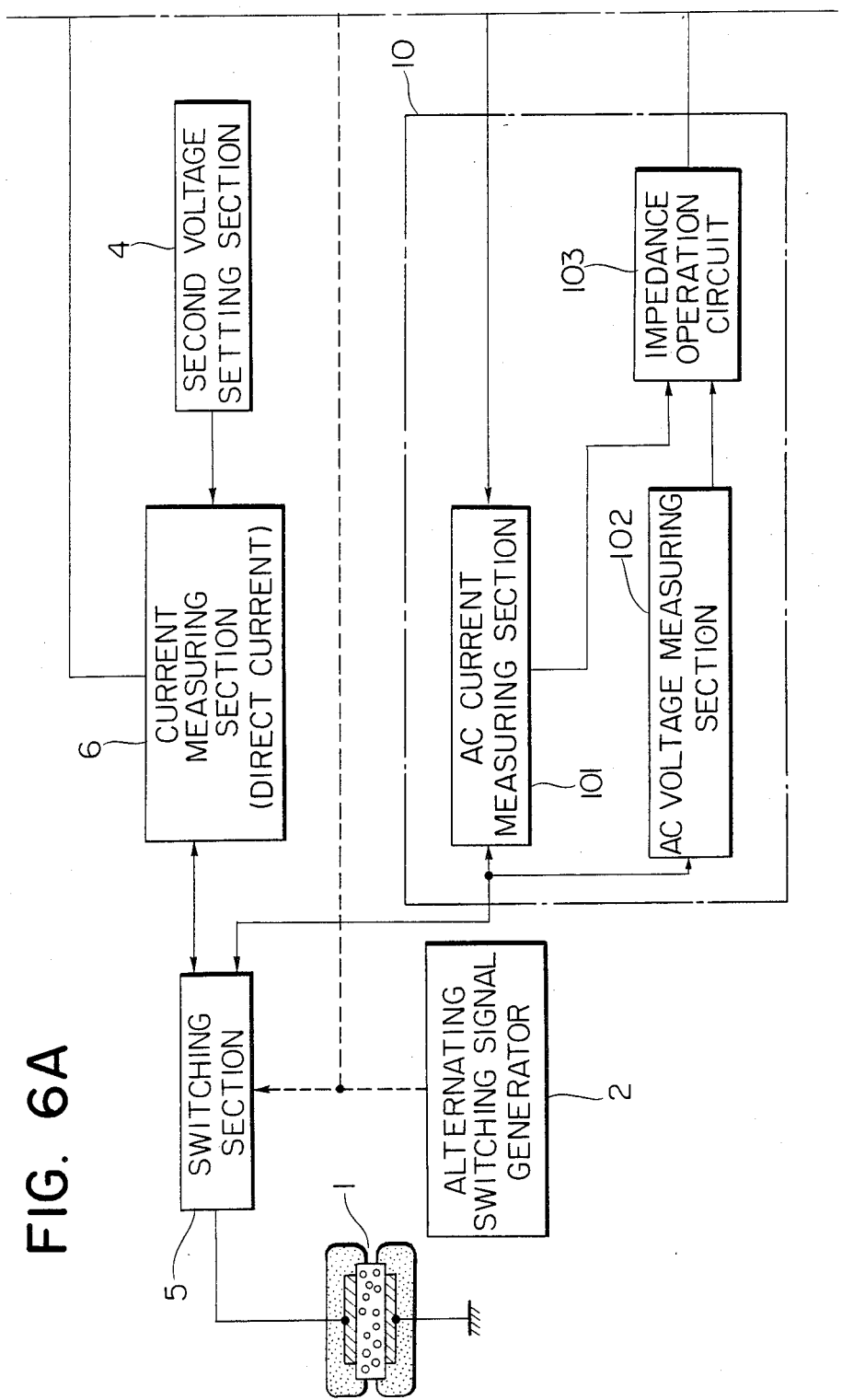
FIGS. 6 to 9 are block diagrams of apparatuses according to other embodiments of the present invention, respectively.

FIG. 6 is a block diagram of an apparatus having an oxygen concentration detecting section for measuring an impedance to detect the oxygen concentration in accordance with the relationship shown in FIG. 5. The same reference numerals used in FIG. 6 denote the same parts as in FIG. 3. An AC voltage having a frequency of 5 Hz to 1 kHz is applied from an AC voltage setting section 12 to a sensor 1, and an impedance measuring section 10 measures an impedance of the sensor 1. The measured impedance is converted by a converter 11 to a signal corresponding to the oxygen concentration in accordance with the relationship shown in FIG. 5. The converted signal is held by a first sample hold section 7. Any other arrangement of this circuit is the same as that shown in FIG. 3. The impedance measuring section 10 comprises an AC current detector 101 for detecting a current flowing through the sensor 1 upon application of an AC voltage, an AC voltage detector 102 for detecting the AC voltage applied across the terminals of the sensor 1, and an impedance operation circuit 103 for calculating the impedance in accordance with the outputs generated from the detectors 101 and 102. The impedance measuring section 10 may be arranged to calculate only the resistance component or the reactance component. An admittance, a conductance or susceptance may be calculated instead of calculating the impedance, its resistance component or its reactance component. When the component to be detected changes, the conversion characteristics of the converter 11 must be changed accordingly.

In the embodiment shown in FIG. 6, an AC component is used to detect only the oxygen concentration. However, an impedance corresponding to the composite concentration of oxygen gas, carbon dioxide gas and steam can also be obtained when an applied voltage is increased.

Figure 7:
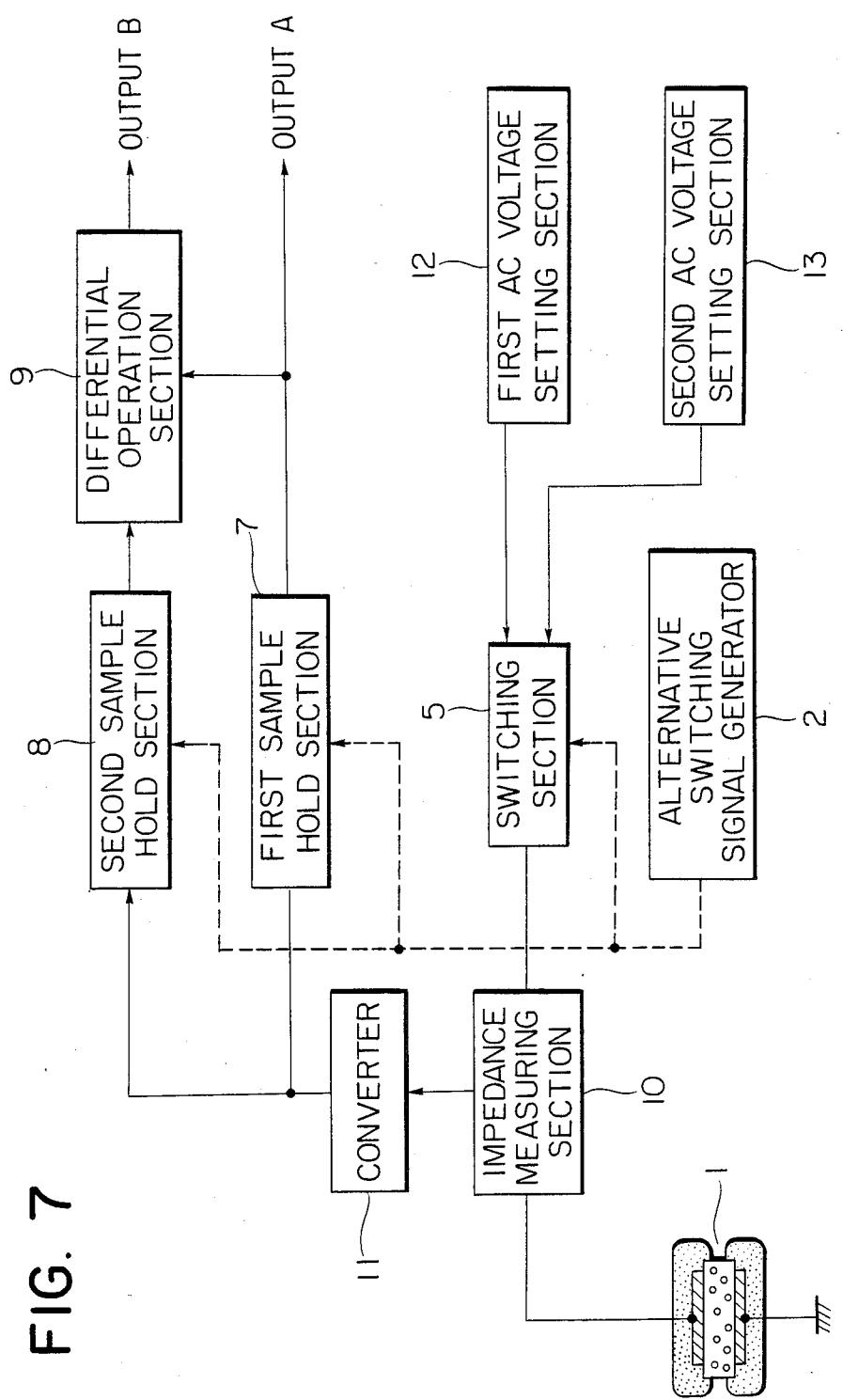

FIG. 7 shows still another embodiment which utilizes this effect. A first AC voltage setting section 12 generates an AC voltage having a voltage of 0.1 mV to 0.5 V and a frequency of 5 Hz to 1 kHz such that its impedance changes in accordance with only the oxygen concentration. The first AC voltage setting section 12 in FIG. 7 has the same arrangement as the AC voltage setting section 12 in FIG. 6. A second AC voltage setting section 13 generates an AC voltage (about 0.6 V to 1.4 V) such that an impedance of the sensor 1 changes in accordance with the composite concentration of $O_2+CO_2+H_2O$ consisting of the oxygen concentration, the carbon dioxide concentration and the steam concentration. Other components such as a switching signal generator 2, a switching section 5, a first sample hold section 7, a second sample hold section 8, a differential amplifier section 9 have the same arrangement and operation mode as those of the embodiment shown in FIG. 3 or 6. An impedance measuring section 10 and a converter 11 in FIG. 7 are the same as those in FIG. 6.

In the embodiment shown in FIG. 7, a relatively high AC voltage from the second AC voltage setting section 13 is used to measure the $O_2+CO_2+H_2O$ concentration. However, this concentration can also be measured by a voltage obtained by superposing a DC bias voltage of about 1 V on a relatively low AC voltage (about 0.1 mV to 0.5 V).

Figure 8:
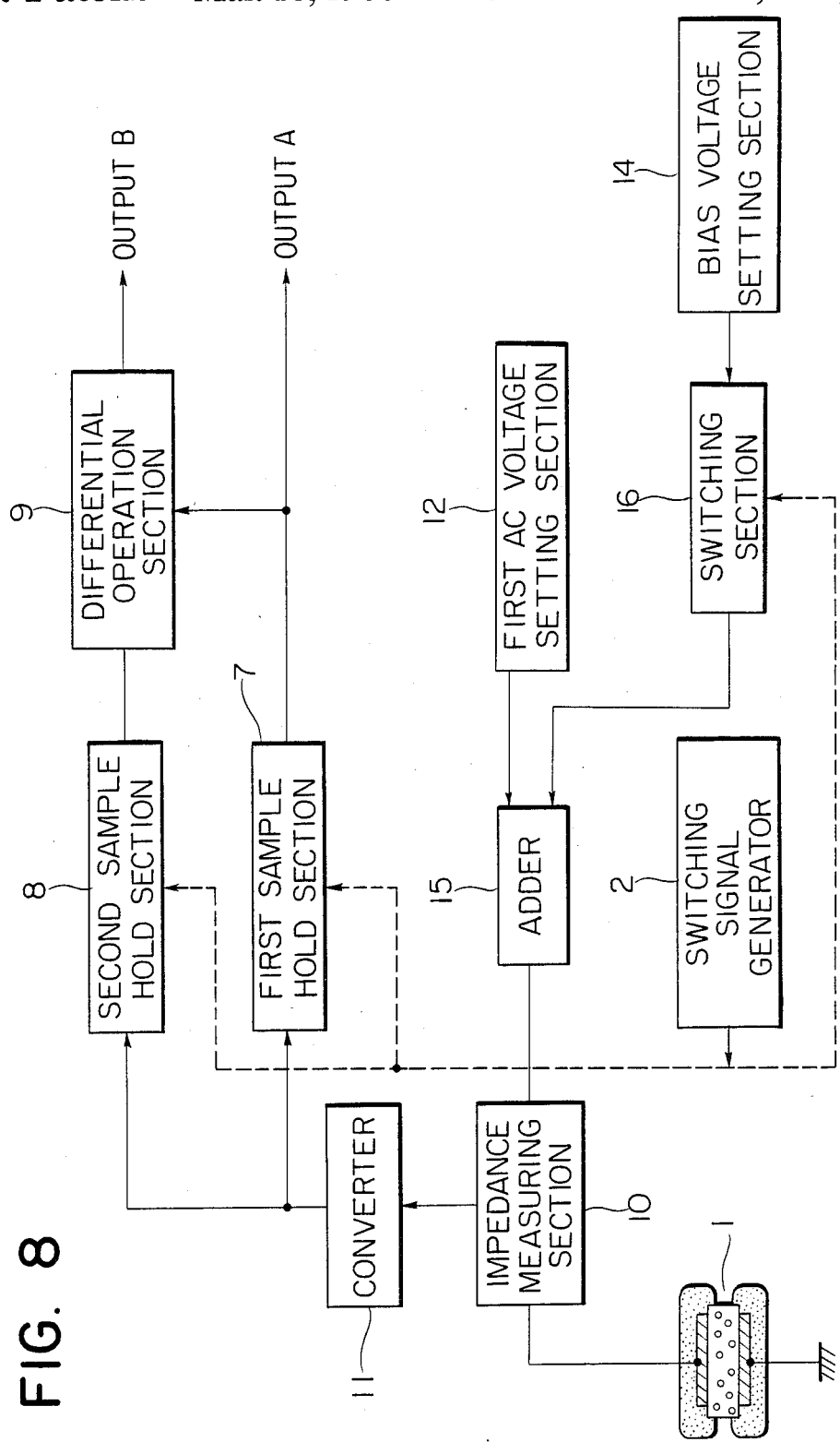

FIG. 8 shows still another embodiment wherein this DC bias voltage is superposed on the relatively low AC voltage to obtain the voltage for measuring the $O_2+CO_2+H_2O$ concentration. In this embodiment, a bias voltage setting section 14, an adder 15, and a switching section 16 are used in place of the second AC voltage setting section 13 and the switching section 5 of FIG. 7. The bias voltage setting section 14 sets a DC voltage of about 1 V. The adder 15 superposes the bias voltage generated from the bias voltage setting section 14 on the AC voltage generated from the first AC voltage setting section 12. The switching section 16 is controlled in response to a signal generated from a switching signal generator 2. The switching section 16 comprises a switch which is disabled while the $O_2$ concentration is detected but which is enabled while the $O_2+CO_2+H_2O$ concentration is detected. When the switching section 16 is turned off, the output from the first AC voltage setting section 12 is applied to the polarographic sensor 1 through the adder 15 and the impedance measuring section 10. The impedance measuring section 10 detects the voltage and current to calculate a corresponding impedance. The impedance signal is converted by the converter 11 to a corresponding $O_2$ concentration. The inverted signal is then held by the first sample hold section 7. While the switching section 16 is kept ON, the output from the first AC voltage setting section 12 is added by the adder 15 to the output generated from the bias voltage setting section 14. The resultant AC-DC signal is applied to the polarographic sensor 1, and the impedance of the sensor 1 is measured by the impedance measuring section 10. The impedance signal representing the concentration of the corresponding gas is converted by the converter 11 to a corresponding concentration signal which is then held by the second sample hold section 8. The differential operator or operation section 9 subtracts the $O_2$ concentration signal held by the first sample hold section 7 from the $O_2+CO_2+H_2O$ concentration signal held by the second sample hold section 8 to generate a signal corresponding to a $CO_2+H_2O$ concentration. This signal appears at an output terminal B. It should be noted that the $O_2$ concentration signal appears at an output terminal A.

Figure 9A:
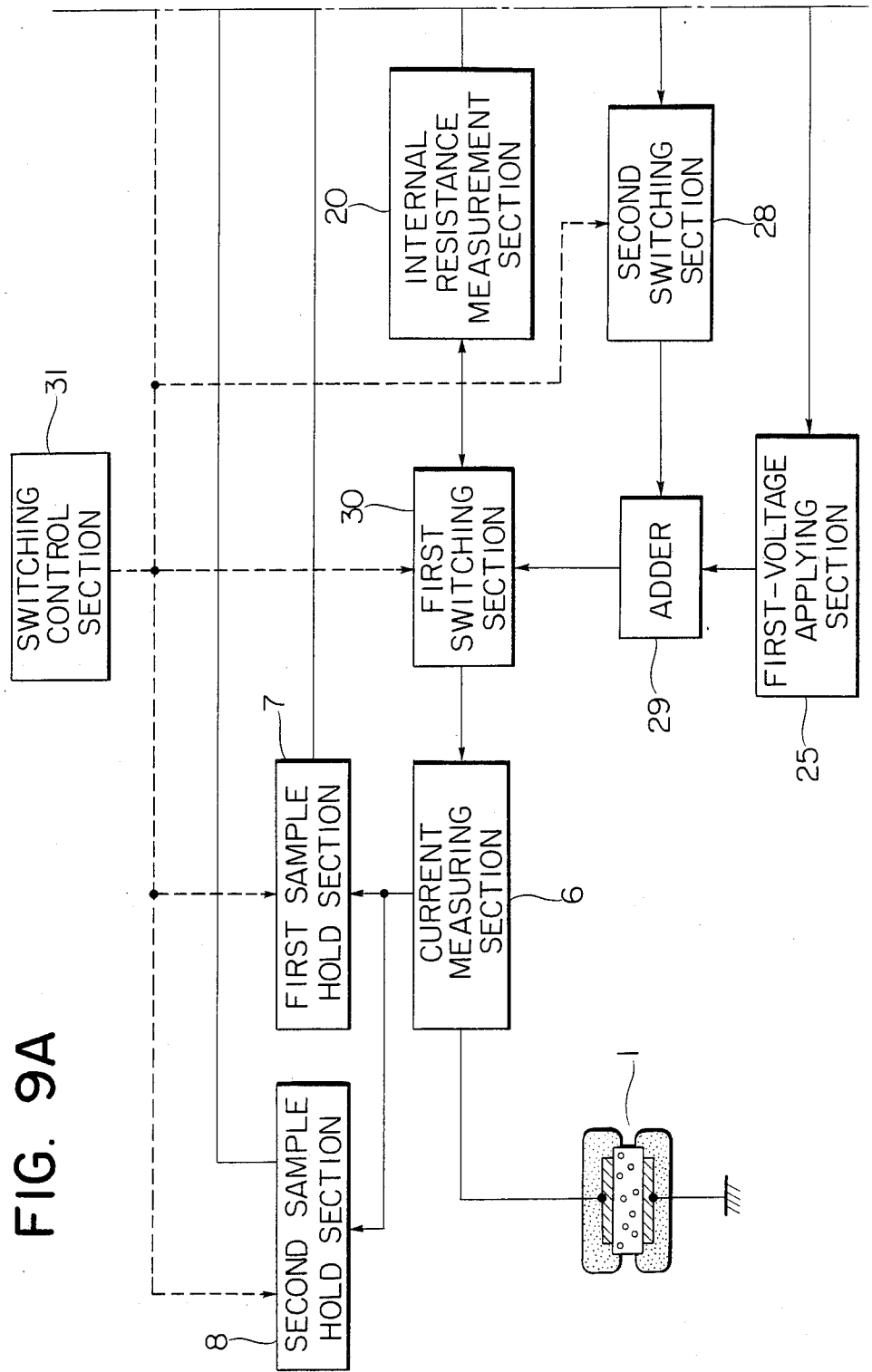

FIG. 9 is a block diagram showing still another embodiment wherein the concentrations are measured upon application of DC voltages in the same manner as in the embodiment shown in FIG. 3. In the embodiment shown in FIG. 9, a time division method with three periods (time slots) is used such that an internal resistance of the polarographic sensor is measured during the first period, an $O_2+CO_2+H_2O$ gas concentration is measured during the second period, and an $O_2$ gas concentration is measured during the third period.

In this embodiment, the technique disclosed in U.S. Ser. No. 373,257 described above is used. More particularly, the DC voltage (to be referred to as a first voltage hereinafter) along the line mn is used detect the $O_2$ concentration. Referring to FIG. 9, a voltage generator for generating a voltage along the line mn comprises an internal resistance detector 20, a third sample hold section 21, a voltage drop calculator 22, an attenuator 23, a predetermined-voltage adder 24 and a first-voltage applying section 25. The first voltage is obtained by adding to a predetermined constant voltage a voltage which corresponds to a voltage drop across the internal resistance of the sensor 1.

The voltage (to be referred to a second voltage) along any one of the lines op, qr, st, and so on for detecting the $O_2+CO_2+H_2O$ concentration in FIG. 1A is obtained such that a constant voltage $V_H$ is applied to a resistor and the resultant variable voltage is added to the first voltage. A second-voltage generator includes a sum voltage setting section 26, a resistor 27, a second switching section 28 and an adder 29. The sum voltage setting section 26 generates the voltage $V_H$ shown in FIG. 1A. The resistor 27 has a resistance to obtain the slope of the lines op, qr, st and so on. The adder 29 adds the first voltage generated from the first-voltage applying section 25 to the voltage obtained through the resistor 27 and generates a sum voltage while the second switching section 28 is kept ON. However, the adder 29 generates the first voltage while the second switching section 28 is kept OFF.

A current detector 6, a first sample hold section 7, a second sample hold section 8, a differential amplifier 9 and so on have the same arrangement and operation mode as those of the embodiment shown in FIG. 3.

A switching control section 31 performs time division. A first switching section 30 is switched between the internal resistance detection mode and the concentration detection mode.

During internal resistance detection, the first switching section 30 is switched to connect the sensor 1 and the internal resistance detector 20. The internal resistance detector 20 measures an internal resistance of the polarographic sensor by applying a very low AC or DC voltage (1 mV to 100 mV) thereto so that the sensor is operated in the resistance control region. A value measured by the detector 20 is sampled and held by the third sample hold section 21.

On the other hand, during $O_2$ concentration detection, the current value obtained during the $O_2$ concentration detection period and held by the first sample hold section 7 is added by the voltage drop calculator 22 to the resistance value held by the third sample hold section 21. The resultant value corresponds to the voltage drop component. This component is partially attenuated by the attenuator 23. The attenuated component is added by the predetermined-voltage adder 24 to the predetermined voltage (about 0.25 V to 1 V), thereby obtaining the voltage (i.e., the first voltage) to be applied during the $O_2$ concentration detection period. The first voltage is applied to the sensor 1 through the first voltage applying section 25. It should be noted that no voltage is superposed to the first voltage by the adder 29 since the second switching section 28 is kept OFF during the $O_2$ concentration detection period.

During the $O_2+CO_2+H_2O$ concentration detection period, the second switching section 28 is turned on, as described above. The first voltage from the first voltage applying section 25 is added by the adder 29 to the voltage (about 0.5 V to 1 V) applied from the sum voltage setting section 26 through the resistor 27, thereby obtaining the second voltage. The second voltage is then applied to the sensor 1, and the $O_2+CO_2+H_2O$ concentration is thus measured.

Unlike the conventional apparatus having a single polarographic solid electrolytic sensor capable of detecting only one component (oxygen gas), according to the present invention described in detail above, voltages having different levels are selectively applied to the polarographic sensor to measure the oxygen concentration and the composite concentration of oxygen gas, carbon dioxide gas and steam, thereby obtaining the composite concentration of carbon dioxide gas and steam. The apparatus of the present invention has a simple, compact, and low cost construction.

What is claimed is:

1. An apparatus for detecting the concentrations of a plurality of gas components, comprising:
    a polarographic solid electrolytic sensor including an oxygen ionic conductor having opposite surfaces, a cathode placed on one surface of said oxygen ionic conductor, an anode placed on the other surface of said oxygen ionic conductor to supply a voltage, and means covering said surfaces where said cathode is placed for regulating the quantity of gas which diffuses toward said cathode;
    first voltage applying means for applying a first voltage to said polarographic sensor so that said polarographic sensor measures only the concentration of oxygen gas;
    second voltage applying means for applying a second voltage, obtained by adding the first voltage and a constant additional voltage, to said polarographic sensor so that said polarographic sensor measures the composite concentration of oxygen gas, carbon dioxide gas and steam;
    said second voltage applying means having an additional voltage setting section for generating an additional voltage, and
    an addition section for adding the additional voltage from said additional voltage setting section and the first voltage from said first voltage applying means to obtain the second voltage;

electric signal detecting means for detecting electric signals from said polarographic sensor when the first and second voltages are applied to said polarographic sensor, respectively, and for generating a signal corresponding to the oxygen concentration and a signal corresponding to the composite concentration of oxygen gas, carbon dioxide gas and steam;

first sample holding means connected to said electric signal detecting means, for storing data corresponding to the signal which corresponds to the oxygen concentration and which is generated from said electric signal detecting means when the first voltage is applied to said polarographic sensor;

second sample holding means connected to said electric signal detecting means, for storing data corresponding to the signal which corresponds to the composite concentration of oxygen gas, carbon dioxide gas and steam and which is generated from said electric signal detecting means when the second voltage is applied to said polarographic sensor; and operating means connected to said first and second sample holding means, for subtracting the signal corresponding to the oxygen concentration from the signal corresponding to the composite concentration of oxygen gas, carbon dioxide gas and steam, and for generating a signal corresponding to a composite concentration of carbon dioxide gas and steam.

2. An apparatus for detecting the concentration of a plurality of gas components, comprising:

a polarographic solid electrolytic sensor including an oxygen ionic conductor having opposite surfaces, a cathode placed on one surface of said oxygen ionic conductor, an anode placed on the other surface of said oxygen ionic conductor to supply a voltage, and means covering said surface where said cathode is placed for regulating the quantity of gas which diffuses toward said cathode;

switching control means for performing a jtime-division switching operation during first time slots for detecting the internal resistance of said polarographic solid electrolytic sensor, second time slots for detecting the concentration of oxygen gas, and third time slots for detecting the composite concentration of oxygen gas, carbon dioxide gas and steam;

internal resistance detecting means for measuring the internal resistance of the polarographic solid electrolytic sensor by applying a voltage thereto so that the sensor is operated in the resistance control region during said first period;

first voltage applying means having a voltage drop calculating section for calculating a voltage drop component caused by the current flowing through said polarographic solid electrolytic sensor in accordance with the internal resistance detected during the first time slots and the current flowing through said polarographic solid electrolytic sensor, an attenuating section for attenuating the output voltage from said voltage drop calculating section, constant voltage adding means for adding the first voltage to the output voltage from said attenuating section and for generating a first voltage having a magnitude which causes said polarographic solid electrolytic sensor to respond only to oxygen gas, and means for applying the output from said constant voltage adding means to said polarographic solid electrolytic sensor during the second time slots under control of said switching control means;

second voltage applying means for applying a second voltage obtained by adding the first voltage and a constant additional voltage to said polarographic sensor so that said polarographic sensor measures the composite concentration of oxygen gas, carbon dioxide gas and steam;

said second voltage applying means having an additional voltage setting section for generating an additional voltage, an addition section for adding the additional voltage from said additional voltage setting section and the first voltage from said first voltage applying means to obtain the second voltage, and a resistor attenuation section, between said additional voltage setting section and said addition section, for attenuating the second voltage set by said second voltage applying means in accordance with change in composite concentration of carbon dioxide gas and steam;

electric signal detecting means for detecting electric signals from said polarographic sensor when the first and second voltages are applied to said polarographic sensor, respectively, and for generating a signal corresponding to the oxygen concentration and a signal corresponding to the composite concentration of oxygen gas, carbon dioxide gas and steam;

first sample holding means connected to said electric signal detecting means, for storing data corresponding to the signal which corresponds to the oxygen concentration and which is generated from said electric signal detecting means when the first voltage is applied to said polarographic sensor;

second sample holding means connected to said electric signal detecting means, for storing data corresponding to the signal which corresponds to the composite concentration of oxygen gas, carbon dioxide gas and steam and which is generated from said electric signal detecting means when the second voltage is applied to said polarographic sensor; and operating means connected to said first and second sample holding means, for subtracting the signal corresponding to the oxygen concentration from the signal corresponding to the composite concentration of oxygen gas, carbon dioxide gas and steam, and for generating a signal corresponding to the composite concentration of carbon dioxide gas and steam.

3. An apparatus according to claim 2, wherein said first and second voltages are direct current voltages, respectively, and said electric signal detecting means comprises means for detecting electric currents from said polarographic sensor.

4. An apparatus according to claim 2, wherein said first voltage falls within the range between 0.2 volts and 0.8 volts and said second voltage falls within the range between 1 volt and 2 volts.

5. An apparatus according to claim 2, wherein at least one of the first and second voltages is an alternating current voltage and said electric signal detecting means comprises means for detecting the impedance of said polarographic sensor when the alternating current voltage is applied to said polarographic sensor.

6. An apparatus according to claim 5, wherein said electric signal detecting means comprises a circuit for calculating the impedance of said polarographic sensor in accordance with the alternating current voltage as the first voltage and a detected alternating current, and a converter for converting the calculated impedance to a signal corresponding to the oxygen concentration.

7. An apparatus according to claim 6, wherein said second voltage is a direct current voltage, and said electric signal detecting means comprises means for detecting electric current from said polarographic sensor.

8. An apparatus according to claim 5, wherein said electric signal detecting means comprises a circuit for calculating the impedance of said polarographic sensor in accordance with the alternating current voltage as the second voltage and a detected alternating current, and a converter for converting the calculated impedance to a signal corresponding to the oxygen concentration.

9. An apparatus according to claim 9, wherein said first voltage is a direct current voltage, and said electric signal detecting means comprises means for detecting electric current from said polarographic sensor.

10. An apparatus according to claim 6, wherein the second voltage is a direct-alternating current superposed voltage obtained by superposing a direct current bias voltage on the alternating current voltage as the first voltage.

11. An apparatus according to claim 2, wherein the first and second voltages are alternating voltages, respectively.

* * * * *